(12) United States Patent
Bernstein

(10) Patent No.: US 8,778,952 B2
(45) Date of Patent: Jul. 15, 2014

(54) METHOD OF REDUCING INTRAOSSEOUS HYPERTENSION

(76) Inventor: Joseph Bernstein, Haverford, PA (US)

(*) Notice: Subject to any disclaimer, the term of this patent is extended or adjusted under 35 U.S.C. 154(b) by 970 days.

(21) Appl. No.: 12/685,195

(22) Filed: Jan. 11, 2010

(65) Prior Publication Data

US 2010/0113455 A1 May 6, 2010

Related U.S. Application Data

(62) Division of application No. 11/941,519, filed on Nov. 16, 2007, now abandoned.

(51) Int. Cl.
*A61K 31/522* (2006.01)
*A61K 31/495* (2006.01)
*A61K 31/53* (2006.01)

(52) U.S. Cl.
USPC .................. 514/263.3; 514/250; 514/243

(58) Field of Classification Search
None
See application file for complete search history.

(56) References Cited

U.S. PATENT DOCUMENTS

| 7,091,207 | B2 | 8/2006 | Kukreja |
| 2004/0038874 | A1 | 2/2004 | Omoigui |
| 2004/0092522 | A1 | 5/2004 | Field et al. |
| 2005/0101673 | A1* | 5/2005 | Norden et al. ................. 514/573 |
| 2006/0004056 | A1 | 1/2006 | Cote et al. |

FOREIGN PATENT DOCUMENTS

| EP | 1953159 A1 | 5/2007 |
| WO | WO 2006016262 A1 | 2/2006 |
| WO | WO 2008112561 A1 | 9/2008 |

OTHER PUBLICATIONS

Morgan ["Radiographic Diagnosis of Joint Disease." in: Radiology of Veterinary Orthopedics: Features of Diagnosis (Napa, Venture Press, 1999), pp. 169-173].*
Mahmud et al. (Journal of Human Hypertension, vol. 15, pp. 707-713; 2001).*
Ho et al. (Orthop Rev., vol. 17, No. 2, abstract; 1988).*
Mayo Clinic reference (Retrieved on Sep. 24, 2011 from the Internet: <URL: http://www.mayoclinic.com/health/osteoarthritis/DS00019).*
Findlay, Rhuematology 2007 (46) 1763-1768.*
Bollet, Annals of Internal Medicine 2001 (134), 591-593.*
Felson et al. Annals of Internal Medicine 2001 (134), 541-549.*
Meizer et al. Wiener Klinische Wochenschrift 2005 (117) 278-286.*
Aigner et al. Foot and Ankle International, 2002 (23) 447-451.*
Ghofrani et al. Journal of the American College of Cardiology 2003 (42) 158-164.*
Leuchte et al. Chest 2004 (125) 580-586; and Foresta et al. European Urology 2007 (51) 1411-1419.*
Foresta et al. European Urology 2007 (51) 1411-1419.*
Jain, Naveen K., et al., Sildenafil-induced peripheral analgesia and activation of the nitric oxide-cyclic GMP pathway, Brain Research, 909 (2001) 170-178, India.
Torres-Lopez, Jorge E., et al., Participation of Peripheral and Spinal Phosphodiesterases 4 and 5 in Inflammatory Pain, Proc. West Pharmacol. Soc. 45: 141-143 (2002), Mexico.
Patil, C.S., et al., Sildenafil induces hyperalgesia via activation of the NO-cGMP pathway in the rat neuropathic pain model, Inflammopharmacology 14 (2006) 22-27, Basel, Switzerland.
Geng, Yu, et al., Cyclic GMP and cGMP-binding Phosphodiesterase Are Required for Interleukin-1-induced Nitric Oxide Synthesis in Human Articular Chondrocytes, The Journal of Biological Chemistry, vol. 273, No. 42, Oct. 16, pp. 27484-27491, 1998, U.S.A.
Simkin, Peter A, Bone pain and pressure in osteoarthritic joints, 2004 Osteoarthritic joint pain, Wiley, Chichester (Novartis Foundation Symposium 260) pp. 179-190.
Deiters, Barthold, et al., Inhibition of hyaluronan export reduces collagen degradation in interleukin-1 treated cartilage, Arthritis Research and Therapy, 2008 Deiters and Prehm, vol. 10, No. 1, Germany.
Pelletier, J.P., J. Maretl-Pelletier, et al., Most recent developments in strategies to reduce the progression of structural changes in osteoarthritis: today and tomorrow, Arthritis Res Ther, 2006, p. 206, 8(2), Montreal, Quebec, Canada.
Felson, D.T., The sources of pain in knee osteoarthritis, Curr Opin Rhematol, 2005, pp. 624-8, 17(5), Lippincott Williams & Wilkins, Boston, MA.
Imhof, H., M. Breitenscher, et al., Degenerative joint disease: cartilage or vascular disease?, Skeletal Radiol, 1997, pp. 398-403, 26(7).
Lehoux, S., Y. Castier, et al., Molecular mechanisms of the vascular responses to haemodynamic forces, J Intern Med, 2006, pp. 381-92, 259(4), Blackwell Publishing Ltd.
Friebe, A., Koesling, D., Regulation of Nitric Oxide-Sensitive Guanylyl Cyclase, Circ Res, 2003, pp. 96-105, 92(2), American Heart Association.
Boswell-Smith, V., Spina, D., et al., Phosphodiesterase inhibitors, Br J Pharmacol, 2006, pp. S252-7, 147 Suppl 1, London, England.
Arnoldi, C.C., Linderholm, H., et al.,Venous Engorgement and Intraosseous Hypertension in Osteoarthritis of the Hip, J Bone Joint Surg Br, 1972, pp. 409-421, 54(3), Umea, Sweden.
Arnoldi, C.C., Lemperg, K., et al., Intraosseous Hypertension and Pain in the Knee, J Bone Joint Surg Br, 1975, pp. 360-363, 57(3), Umea, Sweden.

(Continued)

*Primary Examiner* — Jeffrey S. Lundgren
*Assistant Examiner* — Michael Schmitt
(74) *Attorney, Agent, or Firm* — Caesar, Rivise, Bernstein, Cohen & Pokotilow, Ltd.

(57) ABSTRACT

A method of treating osteoarthritis by reducing intraosseous hypertension in a patient in need thereof by administering to a patient an effective amount of a composition containing a bone edema medication, such as a vasoactive medication or phosphodiesterase inhibitor, including a PDE-5.

20 Claims, 2 Drawing Sheets

(56) References Cited

OTHER PUBLICATIONS

Arnoldi, C.C., Intraosseous Hypertension. A Possible Cause of Law Back Pain?, Clin Orthop Relat Res, 1976, pp. 30-34, (115), Copenhagen, Denmark.

Tsai, C.L, Liu, T.K., Evidence for Eicosanoids Within the Reparative Front in Avascular Necrosis of Human Femoral Head, Clin Orthop Relat Res, 1992, pp. 305-312, (281), Taipei, Taiwan.

Hofmann, S., Engel, A., et al., Bone-Marrow Oedema Syndrome and Transient Osteoporosis of the Hip, Bone Joint Surg Br, 1993, pp. 210-216, 75(2), Vienna, Austria.

Felson, D.T., Chaisson, C.E., et al., The Association of Bond Marrow Lesions with Pain in Knee Osteoarthritis, Ann Intern Med, 2001, pp. 541-549, 134(7).

Bollet, A.J., Edema of the Bone Marrow Can Cause Pain in Osteoarthritis and Other Diseases of Bone and Joints, 2001, Ann Intern Med, pp. 591-593, 134(7).

Uchio, Y., Ochi, M., et al., Intraosseous Hypertension and Venous Congestion in Osteonecrosis of the Knee, Clin Orthop Relat Res, 2001, pp. 217-223, (384), Lippincott Williams & Wilkins, Inc.

Felson, D.T., McLaughlin, S., et al., Bone Marrow Edema and Its Relation to Progression of Knee Osteoarthritis, Ann Intern Med, 2003, pp. 330-336, 139 (5 Pt 1), Boston, MA and Rochester, NY.

Miltner, O., Siebert, C.H., et al., Patellar hypertension syndrome in adolescence: a three-year follow up, Arch Orthop Trauma Surg, 2003, pp. 455-459, 123(9), Springer-Vertag, Germany.

Schneider, T., Drescher, W., et al., the impact of vasoactive substances on intraosseous pressure and blood flow alterations in the femoral head: a study based on magnetic resonance imaging, Arch Orthop Trauma Surg, 1998, pp. 45-49, 118(1-2), Springer-Vertag, Germany.

Tenor, H., Hedbom, E., et al., Phosphodiesterase isoenzyme families in human osteoarthritis chondrocytes—functional importance of phosphodiesterase 4, Br J Pharmacol, 2002, pp. 609-618, 135(3), Nature Publishing Group.

Gauthier, J.V., Barbosa, L.M., Bone Pain in Transplant Recipients Responsive to Calcium Channel Blockers, Ann Inter Med, 1994, pp. 863-865, 121(11), Seattle, WA.

Niemi, K. et al., Standardized Vasoactive Medications: A Unified System for Every Patient, Everywhere, Nospital Pharmacy, 2005, pp. 984-993, 40: 11.

Felson, D.T., Clinical practice. Osteoarthritis of the Knee, N. Engl J Med, 2006, pp. 841-849, 354(8), USA.

Corbin et al. Cyclic GMP Phosphodiesterase-5: Target of Sildenafil. J. Biol. Chem. 1999, 274:13729-13732.

Ghofrani et al. Sildenafil for treatment of lung fibrosis and pulmonary hypertension: a randomized controlled trial. Lancet. 360 (2002) pp. 895-900.

Raisz et al. Prostaglandin synthesis by fetal rat bone in vitro: Evidence for a role of prostacyclin. Prostaglandins, vol. 17, Issue 6, Jun. 1979, pp. 905-914.

Cooper. Proc Bayl Univ Med Cent. 2011;24(2):115-118.

Schermuly et al. Iloprost-induced desensitization of the prostacyclin receptor in isolated rabbit lungs. Respiratory Research 2007, 8:4, 1-13.

\* cited by examiner

METHOD OF REDUCING INTRAOSSEOUS HYPERTENSION

FIELD OF THE INVENTION

The present invention generally relates to the fields of orthopedics and rheumatology and, in particular, to a treatment for bone pain associated with osteoarthritis and related conditions. More specifically, the present invention relates to a method of treating pain caused by osteoarthritis with bone edema medications. Medications that may be used according to the present invention include vasoactive medications, such as phosphodiesterase inhibitors, which modulate blood flow to bone of a patient in the vicinity of an arthritic joint to affect the physiology of the bone in a manner that leads to a reduction in the pain associated with osteoarthritis.

BACKGROUND OF THE INVENTION

Osteoarthritis is the most common musculoskeletal and joint diseases in the world. Because medical advances have increased the average lifespan, yet have not devised an effective means of preventing wear and tear of the joints, osteoarthritis is rapidly becoming a significant medical and financial burden to the world (Pelletier et al. 2006) and is a leading cause of impaired mobility in the elderly. (Felson 2006). Osteoarthritis is a condition of primary failure of articular cartilage, which is accompanied by subchondral hardening of bone, osteophytes (bone spurs) at the joint margin, juxtaarticular bone cysts, and joint space narrowing. Pain is the most prominent and disabling symptom of osteoarthritis. (Felson 2005). Osteoarthritis usually develops in the smaller joints of the fingers, the weight-bearing joints of the leg, and the movable portions of the spine, although any diarthrodial joint can be affected.

Osteoarthritis was long thought to reflect the aging process, in which repetitive use of joints results in cartilage erosion. And whereas it is true that osteoarthritis is characterized by cartilage loss, cartilage damage cannot be the source of the pain, as there are no pain fibers in articular cartilage, and in some patients cartilage loss may occur without any accompanying symptoms. (Felson 2005). As more is understood about the molecular structure and function of cartilage, the pain associated with osteoarthritis appears to be the result of a complex interplay between mechanical, cellular, and biochemical forces.

At present, there are no means to effectively restore damaged articular cartilage to its healthy state, i.e., once damaged, human adult cartilage remains damaged for life. Thus, the primary goals of treatment of osteoarthritis are to help patients understand their disease, relieve their pain, minimize their disability, and limit the progression of their disease. Medical treatment of osteoarthritis often involves administration of pain relievers such as acetaminophen or aspirin. Alternatively, nonsteriodal anti-inflammatory drugs (NSAIDs), such as ibuprofen, nabumetone or naproxen, amongst others, may be administered. Although these drugs act to "block" the pain and/or reduce inflammation, they do not affect the physiology underscoring and producing the pain. Such an approach is suggested by the instant invention.

Articular cartilage itself is relatively avascular, and lacks pain receptors. Thus, although osteoarthritis represents a failure of cartilage, the pain cannot and does not originate from the damaged cartilage itself. Rather, the pain can be mediated by the only peri-articular structures which possess the neural apparatus for sensing pain (i.e., nociceptors): namely, the synovium and the bone underlying the cartilage. It is only those structures (alone or in combination) that can be responsible for the sensation of pain experienced by patients suffering from osteoarthritis.

There is clinical evidence suggesting that pressure within the bone may contribute, at least in part, to joint pain. For example, the medical literature has discussed a case in which Dr. Scott Dye of San Francisco injected his own bone with saline under pressure, in the name of science. He experienced pain which lasted for a year.

Also, more than 30 years ago, it was observed that pain due to severe osteoarthritis may be associated with "intraosseous hypertension," i.e., pressure within the bone. (Arnoldi et al. 1975). Intraosseous hypertension is the manifestation of edema within the bone. Thus, it has been proposed that local vascular changes may be important in the pathogenesis of degenerative arthritis and the production of its associated symptoms. (Arnoldi et al. 1972). It has been further observed that surgical decompression of bone (specifically in the case of osteonecrosis) can relieve bone pain. Use of surgery, however, to alleviate pressure within the bone is not ideal. For one thing, surgery can produce myriad side effects and complications, but more to the point, the problem with surgical decompression is that its benefit will be transient. The fenestrations created during so-called decompressive procedures are bound to fill with fibrocartilage. Thus, there is an ongoing need for a safe and effective method for alleviating pressure in bone causing joint pain, most typically found in patients suffering from osteoarthritis.

SUMMARY OF THE INVENTION

It is an object of this invention to provide a method of treating pain associated with osteoarthritis. It is another object of this invention to provide a method of treating intraosseous hypertension associated with osteoarthritis. It is a further object of this invention to provide a method of treating osteoarthritis. The present invention includes a method of treating bone pain associated with osteoarthritis and other conditions by administering to a patient a therapeutically effective amount of a pharmaceutically acceptable bone edema medication. Bone edema medications used according to the present invention include vasoactive medications such as phosphodiesterase inhibitors. According to an aspect of the present invention, a therapeutically effective amount of a subtype 5 phosphodiesterase enzyme (PDE5) selective inhibitor, such as avanafil, sildenafil, tadalafil, udenafil, vardenafil and zaprinast, may be administered. The medication is administered in an amount sufficient to reduce pain associated with osteoarthritis and may be administered, for example, via intravenous, transdermal or oral routes. Further, the medication may be administered in combination with other medications. The patient may be a human or a non-human mammal.

BRIEF DESCRIPTION OF SEVERAL VIEWS OF THE DRAWINGS

The invention will be described in conjunction with the following figures in which like reference numerals designate like elements and wherein.

DETAILED DESCRIPTION OF THE INVENTION

Figure 1:
FIG. 1 is a coronal view of a magnetic resonance image (MRI) scan of a patient's arthritic knee prior to routine administration of a phosphodiesterase inhibitor.

The present invention provides methods of treating bone pain by administering to a patient an effective amount of a pharmaceutically acceptable bone edema medication. In accordance with the present invention, bone edema medications, including vasoactive medications and phosphodiesterase inhibitors, are administered to a patient suffering from pain, e.g. joint pain from osteoarthritis. Bone edema medications of the present invention reduce or eliminate intraosseous hypertension in the bone, within the vicinity of the affected joint, by altering vascular profusion (blood flow in and out of the bone), thereby reducing bone edema. By reducing or eliminating intraosseous hypertension, the method of the present invention reduces or eliminates a source of pain for osteoarthritis sufferers.

Phosphodiesterases (PDE) are a diverse family of enzymes that hydrolyze cyclic nucleotides and thus play a key role in regulating intracellular levels of second messangers—adenosine monophosphate (cAMP) and guanosine monophosphate (cGMP)—and hence cell function. (Boswell-Smith et al. 2006). PDE activity is found in every cell in the body, although there is distinct cellular and subcellular distribution of eleven isoenzymes, which has provided many possibilities for selective therapeutic targets. Isoenzyme selective targets have been identified for specific diseases. For example, the subtype 3 phosphodiesterase enzyme PDE-3 selective inhibitors have been used to treat cardiovascular disease, asthma, congestive heart failure, to relax vascular and airway smooth muscle, inhibit platelet aggregation, and induce lipolysis. (Boswell-Smith et al. 2006). PDE-4, a cAMP-specific PDE, is the predominant isoenzyme in the majority of inflammatory cells, with the exception of platelets, implicated in inflammatory airways disease. There is a current resurgence underway in the development of PDE-4 inhibitors to treat central nervous system indications such as memory enhancement. The PDE-5 enzyme catalyzes the breakdown of the smooth muscle relaxing agent cGMP (U.S. Pat. No. 7,091,207) making it a cGMP-specific PDE. Those of ordinary skill in the art will recognize that many compounds exist which are inhibitors of PDE-5 including, sildenafil (marketed as Viagra®), vardenafil (marketed as Levitra®), tadalafil (marketed as Cialis®), ananafil, udenafil, zaprinast, and the like.

The inventor has discovered that exposure to a PDE-5 inhibitor reduces or eliminates the pain associated with osteoarthritis. Accordingly, in one embodiment of the present invention, the PDE-5 inhibitor that is employed in the practice of the present invention is sildenafil (Viagra®). Sildenfil is the first oral agent approved for treatment of erectile function in men. (U.S. Pat. No. 7,091,207). Its method of action is understood to be as follows: Sexual stimulation results in the release of nitric oxide from nerves and endothelial cells in the corpus cavernosum of the penis, which in turn stimulates guanylate cyclase with subsequent formation of cGMP. Accumulation of cGMP leads to smooth muscle cell relaxation in the arteries, arterioles and sinusoids in the corpus cavernosum, allowing this erectile tissue to fill with blood and causing erection. Men with erectile dysfunction may be unable to maintain adequate amounts of cGMP because it is broken down by PDE-5, which is found in high levels in the genetalia. By inhibiting PDE-5, sildenafil allows an increase in cGMP concentration and improved vasodilation, thus facilitating erection.

Without being bound by theory, in the practice of the present invention, the vasodilatory action of PDE-5 inhibitors such as sildenafil may function by affecting the muscle tone of blood vessels, thereby altering blood flow. By modulating the blood flow to bone of a patient suffering from joint pain with a PDE-5 inhibitor, the intraosseous pressure resulting from the buildup of bone edema will be alleviated, thereby palliating joint pain.

In other embodiments of the invention, the PDE-5 inhibitors are vardenafil and tadalafil, which are also used for treatment of erectile dysfunction in men. However, the present invention is not limited to phosphodiesterase inhibitors specifically recited herein but also includes other phosphodiesterase inhibitors and vasoactive medications which cause alterations in the inflow and outflow of blood to bone. The broad concept of the present invention includes the administration of any bone edema medication which reduces or eliminates intraosseous hypertension, including those not yet discovered, such as, but not limited to, injectable dosage forms and solid dosage forms such as tablets, capsules, and the like.

The medications used in the practice of the present invention may be administered as a pharmaceutical preparation comprising a pharmaceutically acceptable carrier. Such a pharmaceutical preparation may be in any of many forms known to be suitable for administration of drugs. The medications may be administered in the pure form or in a pharmaceutically acceptable formulations including suitable elixirs, binders, and the like, or as pharmaceutically acceptable salts or other derivatives (e.g., sildenafil citrate). It should be understood that the pharmaceutically acceptable formulations and salts include liquid and solid materials conventionally utilized to prepare injectable dosage forms and solid dosage forms such as tablets and capsules. Water may be used for the preparation of injectable compositions which may also include conventional buffers and agents to render the injectable composition isotonic. Other potential additives include colorants, surfactants, binders and encapsulants, diluents, excipients, disintegrating agents, coatings, preservatives and the like.

Depending on the formulation, it is expected that the active agent (e.g., PDE-5 inhibitor) will comprise 1-99% of the composition and carrier will constitute 1-99% of the composition. Such pharmaceutical compositions may include any suitable pharmaceutically acceptable additives or adjuncts to the extent that they do not hinder or interfere with the desired therapeutic effect of the medication.

Those of ordinary skill in the art will recognize that the exact dosage of the medication to be administered may vary depending on factors such as the age, gender, weight and health status of the individual patient, as well as on the precise nature of the condition being treated. Similarly, the length of duration of the treatment with the medication will vary from patient to patient, and will depend on the application of the medication. In all cases, the amount of medication to be administered and the precise treatment protocol should be determined by a skilled practitioner such as a physician.

The preferred dosage of medication required to practice methods of the present invention, i.e., the quantity sufficient to carry out the method, is about the same as or less than that which is normally or typically administered for previously known uses or applications of the medication, i.e., PDE-5 inhibitors for treating male erectile dysfunction. For example, to elicit a reduction in pain associated with osteoarthritis, a regular dose of 50 mg or less of Viagra® is expected to be at least temporarily effective for most patients.

The medication may be administered by any of a wide variety of means which are well known to those of ordinary skill in the art including, but not limited to, intravenously, intramuscularly, orally, rectally, and the like, or by other routes including, but not limited to, transdermal, sublingual, aerosol, etc., which is suitable for the particular means of administration.

Further, the medications of the present invention may be administered either alone or together with other medications in a treatment protocol. For example, a PDE-5 inhibitor may be administered either separately or in combination with other osteoarthritis drugs.

While in some embodiments, the patient that is treated by the methods of the present invention are human in origin, this need not be the case. Those of ordinary skill in the art will recognize that other mammals may also benefit from the methods of the present invention. Thus, veterinarian applications are also contemplated. Further, patients treated with medications according to the methods of the present invention may be in any stage of life, e.g., new-born, adult or aging, although as previously mentioned, osteoarthritis is considered to be primarily a disease of the elderly.

The invention will be illustrated in more detail with reference to the following Example, but it should be understood that the present invention is not deemed to be limited thereto.

EXAMPLE

A physician, who is also the inventor of the present invention, performed an arthroscopic surgical procedure on a male patient suffering from a loose cartilage body in the setting of severe arthritis in his knee. The patient was a competitive senior tennis player and declined knee replacement for that reason. The purpose of the procedure was merely to remove a loose body and abate the mechanical symptoms it caused. Prior to the procedure, an MRI of a coronal view of the patient's knee was taken, as shown in FIG. 1.

Figure 2:
FIG. 2 is a coronal view of an MRI of the same patient's knee as in FIG. 1, after routine administration of a phosphodiesterase inhibitor.

Approximately one year later, the patient returned to his physician for evaluation of what was believed to be an unrelated ganglion cyst on the same knee. To evaluate this cystic mass, another MRI of a coronal view of the patient's knee was taken, as shown in FIG. 2. The patient had reported that over the few months prior to the second MRI but well past the surgical procedures, his pain from his knee arthritis had significantly improved. He inquired whether the more recent MRI (FIG. 2) revealed why this was so. The patient's physician and a senior radiologist compared the earlier MRI (FIG. 1) to the later MRI (FIG. 2), and observed that the earlier MRI (FIG. 1) showed white spots on the patient's tibial spines, whereas the later MRI (FIG. 2) revealed that the white spots had dissipated or resolved. The physician and a radiologist noted that the high signal shown in the MRI of FIG. 1 represents bone edema, and hence, intraosseous hypertension. They further noted that the MRI of FIG. 2, as compared with that of FIG. 1, showed a resolution of the edema, and that although the radiographs were otherwise unchanged, the patient's symptoms were markedly reduced. The physician therefore concluded that the patient had intraosseous hypertension which was shown to have dissipated or have been resolved by the time of the MRI of FIG. 2.

Upon questioning by his physician, the patient explained that the only difference in his medical history (including lifestyle, activity, new illness and medications) between the time of the first and second MRIs was that he started using a phosphodiesterase inhibitor. Specifically, the patient started using Viagra® (50 mg of sildenafil, once per day). There were no other changes in the interval medical history. The physician inferred that reduction in knee pain experienced by the patient was the result of the dissipation of the intraosseous hypertension which, in turn, was the result of using a phosphodiesterase inhibitor.

While the invention has been described in detail in terms of its preferred embodiments and with reference to the above example, it will be apparent to those skilled in the art that the invention can be practiced with modification within the spirit and scope of the appended claims. Accordingly, the present invention should not be limited to the embodiments as described above, but should further include all changes, modifications and equivalents thereof within the spirit and scope of the description provided herein.

What is claimed is:

1. A method for reducing intraosseous hypertension in a patient in need thereof comprising administering to the patient a therapeutically effective amount of a subtype 5 phosphodiesterase enzyme (PDE5) selective inhibitor selected from the group consisting of sildenafil, tadalafil, vardenafil, and combinations thereof.

2. The method of claim 1, wherein the step of administering is via an intramuscular route.

3. The method of claim 1, wherein the step of administering is via an oral route.

4. The method of claim 1, wherein the step of administering is via an intravenous route.

5. The method of claim 1, wherein the patient is a human.

6. The method of claim 1, wherein the patient is a non-human mammal.

7. The method of claim 1, wherein the step of administering is via aerosol.

8. A method for retarding the progression of osteoarthritis by reducing intraosseous hypertension in a patient in need thereof comprising administering to the patient a therapeutically effective amount of a subtype 5 phosphodiesterase enzyme (PDE5) selective inhibitor selected from the group consisting of sildenafil, tadalafil, vardenafil, and combinations thereof.

9. The method of claim 8, wherein the step of administering is via an intramuscular route.

10. The method of claim 8, wherein the step of administering is via an oral route.

11. The method of claim 8, wherein the step of administering is via an intravenous route.

12. The method of claim 8, wherein the patient is a human.

13. The method of claim 8, wherein the patient is a non-human mammal.

14. The method of claim 1, wherein the step of administering is via aerosol.

15. A method for reducing intraosseous hypertension in a patient in need thereof comprising administering to the patient a therapeutically effective amount of sildenafil.

16. A method for treating bone edema a patient in need thereof comprising administering to the patient a therapeutically effective amount of sildenafil.

17. A method for reducing intraosseous hypertension in a patient in need thereof comprising administering to the patient a therapeutically effective amount of tadalafil.

18. A method for treating bone edema a patient in need thereof comprising administering to the patient a therapeutically effective amount of tadalafil.

19. A method for reducing intraosseous hypertension in a patient in need thereof comprising administering to the patient a therapeutically effective amount of vardenafil.

20. A method for treating bone edema a patient in need thereof comprising administering to the patient a therapeutically effective amount of vardenafil.

* * * * *